(12) United States Patent
Van Remoortere et al.

(10) Patent No.: US 9,321,758 B2
(45) Date of Patent: Apr. 26, 2016

(54) AMORPHOUS SALT OF A MACROCYCLIC INHIBITOR OF HCV

(75) Inventors: Peter Jozef Maria Van Remoortere, Princeton, NJ (US); Roger Petrus Gerebern Vandecruys, Westerlo (BE); Herman De Kock, Arendonk (BE)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 609 days.

(21) Appl. No.: 13/202,166

(22) PCT Filed: Feb. 26, 2010

(86) PCT No.: PCT/EP2010/001197
§ 371 (c)(1),
(2), (4) Date: Aug. 18, 2011

(87) PCT Pub. No.: WO2010/097229
PCT Pub. Date: Sep. 2, 2010

(65) Prior Publication Data
US 2011/0306634 A1    Dec. 15, 2011

(30) Foreign Application Priority Data
Feb. 27, 2009    (EP) .................................. 09153964

(51) Int. Cl.
*A61K 9/00*    (2006.01)
*A61K 31/33*    (2006.01)
(Continued)

(52) U.S. Cl.
CPC ................ *C07D 417/04* (2013.01); *A61K 9/14* (2013.01); *A61K 31/4725* (2013.01)

(58) Field of Classification Search
CPC .............................. A61K 9/14; A61K 31/4725
USPC ............................ 424/400; 514/183, 311, 312
See application file for complete search history.

(56) References Cited
U.S. PATENT DOCUMENTS
2008/0146809 A1 *    6/2008    Satyanarayana et al. ..... 546/174

FOREIGN PATENT DOCUMENTS
CN    1938311 A    3/2007
EA    200800482    7/2006
(Continued)

OTHER PUBLICATIONS
Berge, "Pharmaceuticals Salts", Journal of Pharmaceutical Science, vol. 66, No. 1, pp. 1-19, (1977).
(Continued)

*Primary Examiner* — Shengjun Wang
(74) *Attorney, Agent, or Firm* — Andrea Jo Kamage

(57) ABSTRACT

The amorphous form of the sodium salt of the macrocyclic inhibitor of HCV of formula:

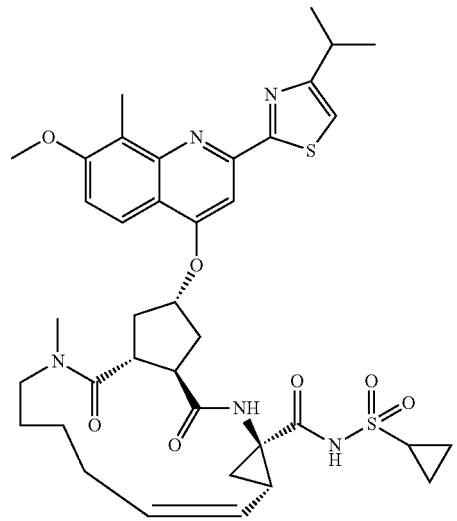

as well as processes for manufacturing this salt.

3 Claims, 7 Drawing Sheets

(51) Int. Cl.
*A61K 31/47* (2006.01)
*C07D 417/04* (2006.01)
*A61K 9/14* (2006.01)
*A61K 31/4725* (2006.01)

(56) References Cited

FOREIGN PATENT DOCUMENTS

| JP | 2008-115173 A | 5/2008 |
| JP | 2009-137934 A | 6/2009 |
| WO | WO 2005/073216 A2 | 8/2005 |
| WO | WO 2005/095403 A2 | 10/2005 |
| WO | WO 2007/014926 A1 | 2/2007 |
| WO | WO 2007/014927 A2 | 2/2007 |
| WO | WO 2008/073195 A1 | 6/2008 |
| WO | WO 2008/092954 A2 | 8/2008 |
| WO | WO 2009/027811 A | 3/2009 |

OTHER PUBLICATIONS

Gould, "Salt Selection for Basic Drugs", International Journal of Pharmaceutics, vol. 33, No. 1/03, pp. 201-217, (1986).
Khimicheskay Entsiklopediya, Moscow, 1995, V. 4, pp. 376 and 377.
Ministry of Health, Labour and Welfare, Notification No. 568 of the Evaluation and Licensing Division, "Settings of Specification and test methods of new drugs", PMSB dated May 1, 2001.
Chinese Search Report for App No. 2010800099089 dated Jul. 9, 2013.
Japanese Office Action for App No. 2011-551440 dated Mar. 26, 2014.
Russian Office Action for App No. 2011139325/04 dated Jun. 25, 2013.

* cited by examiner

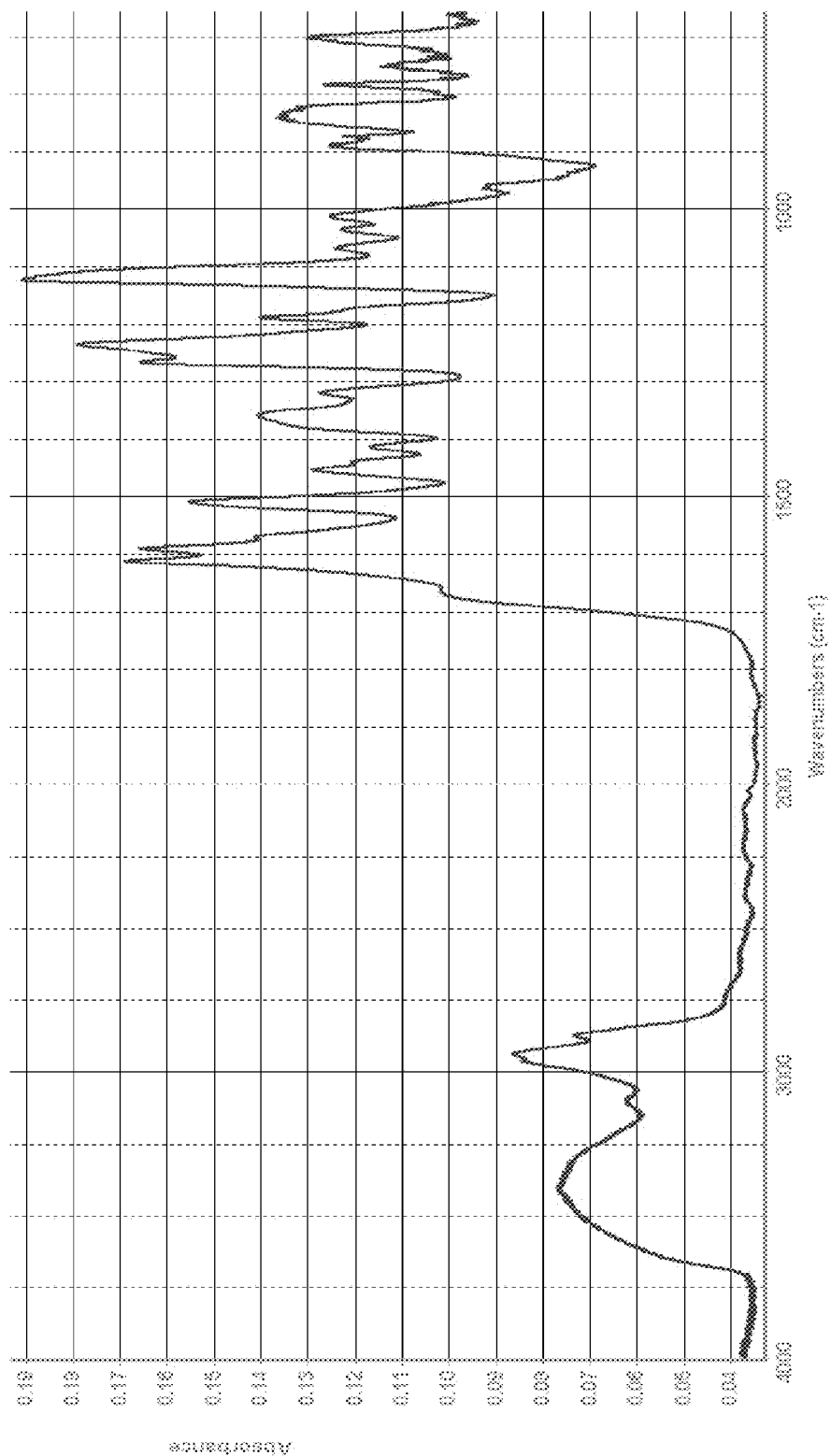
Figure 1: Infrared spectrum (microATR) of TMC435 Na salt

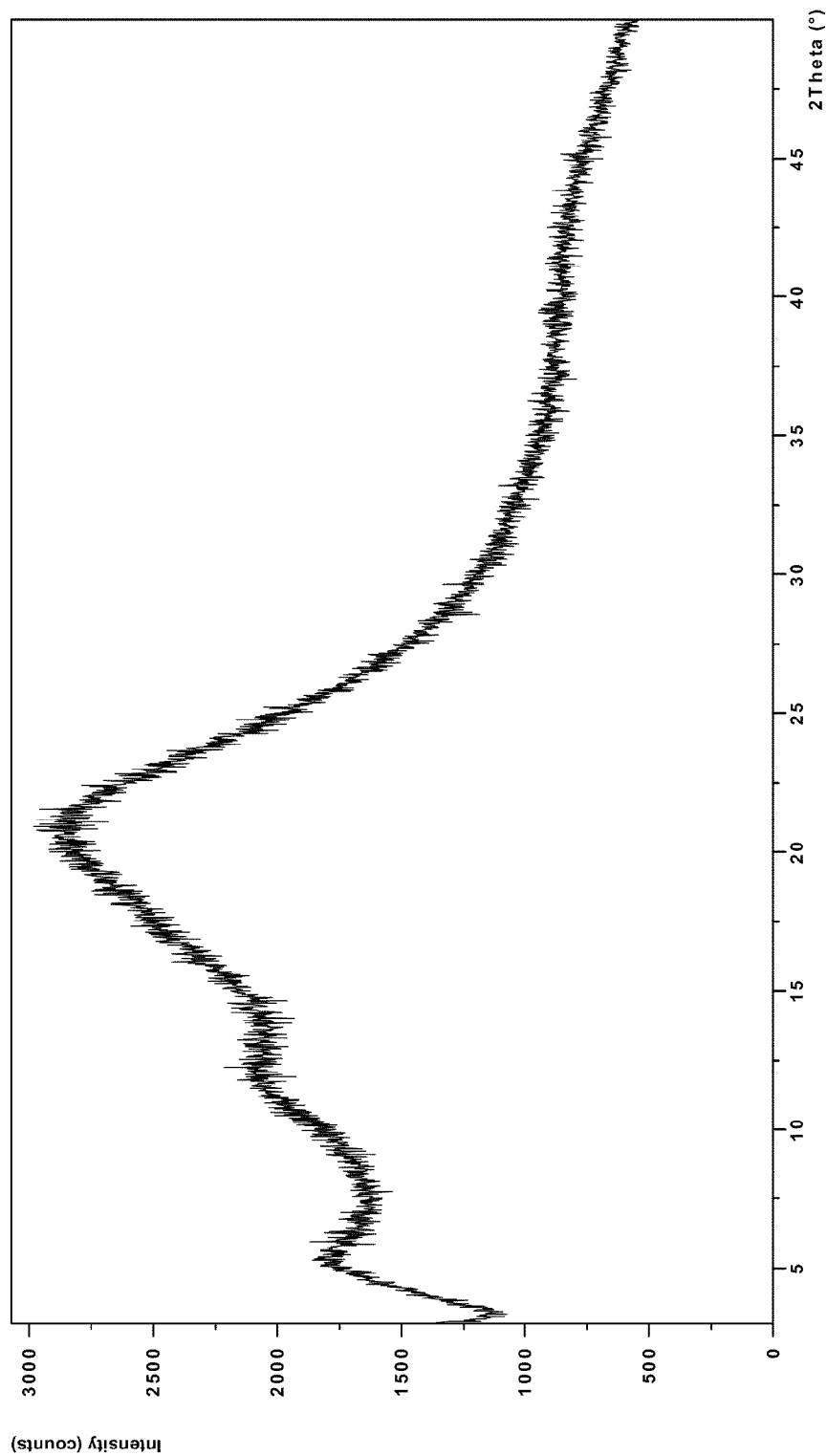
Figure 2: Powder XRD pattern of TMC435 Na salt.

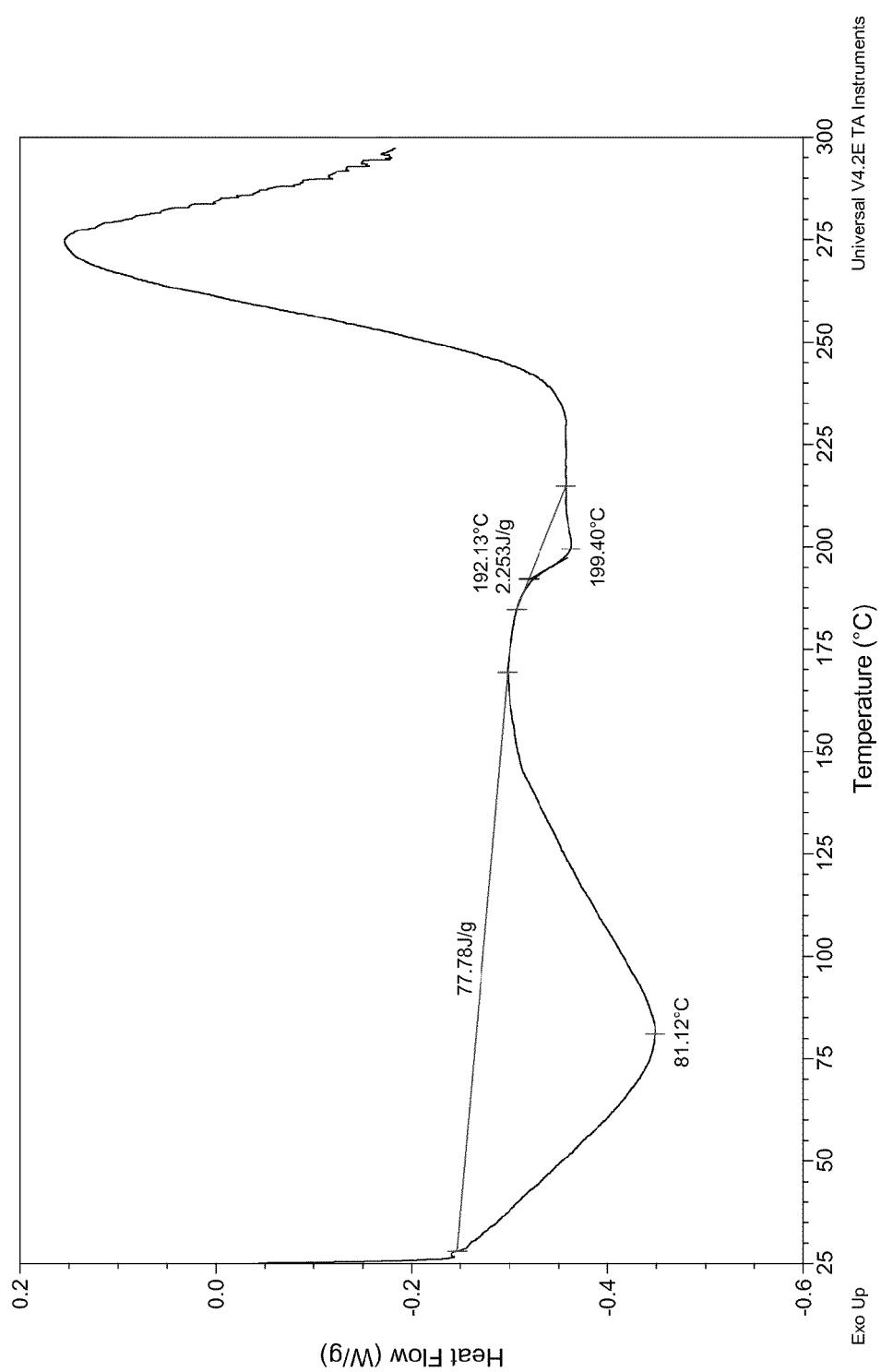
Figure 3: DSC curve of TMC435 Na salt

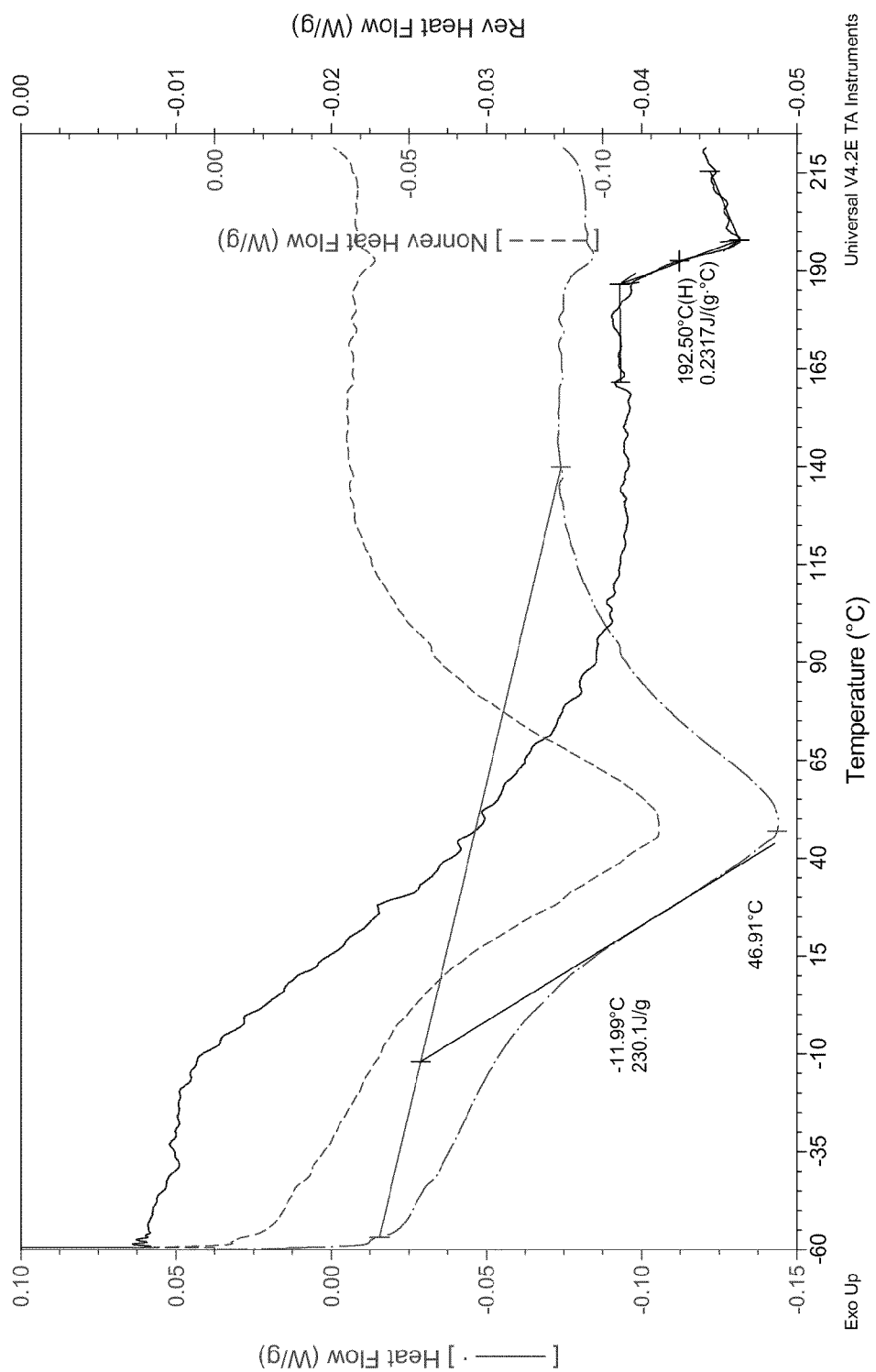
Figure 4: MDSC overlay of TMC435 Na salt

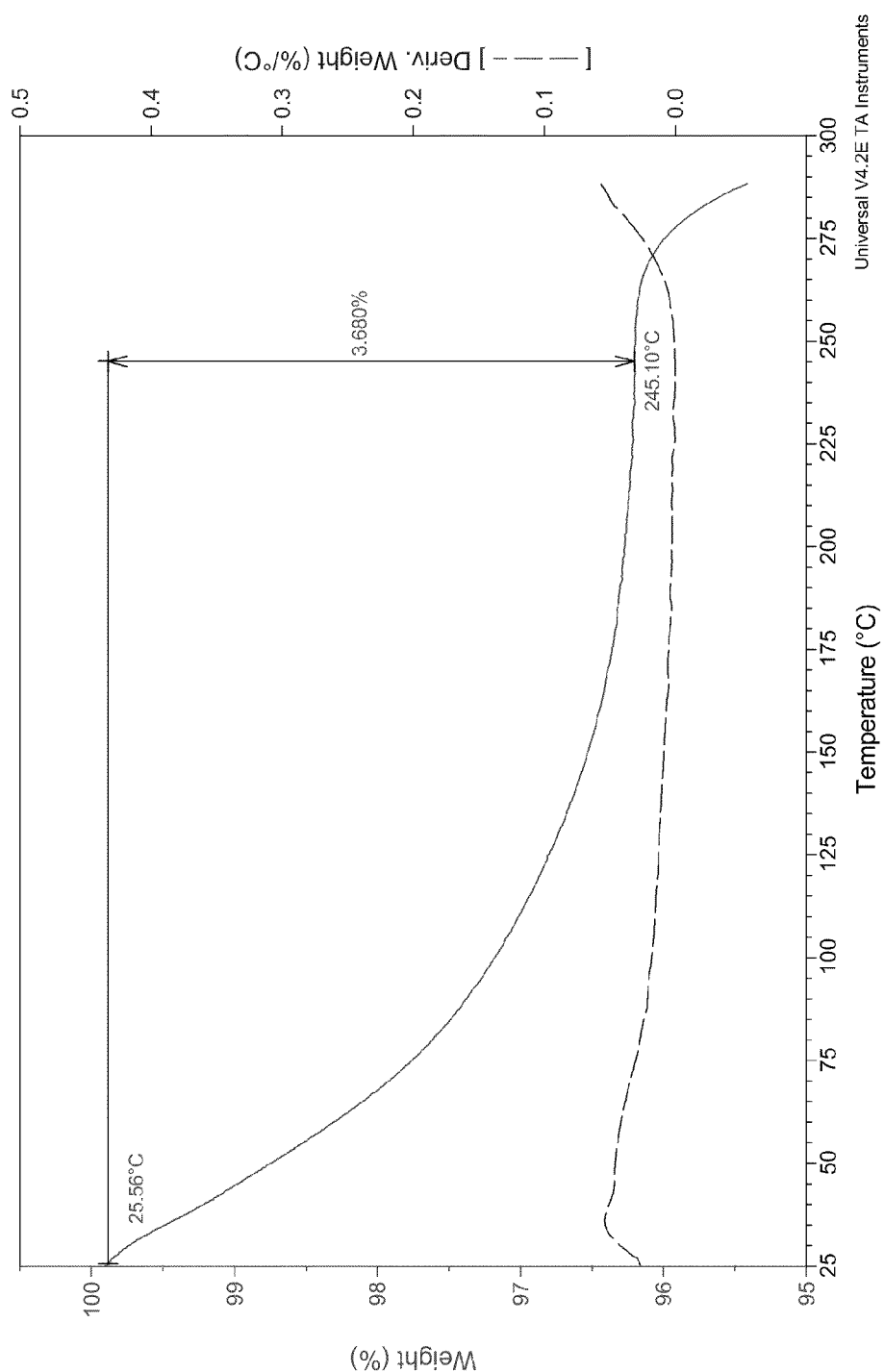
Figure 5: TGA curve of TMC435 Na salt

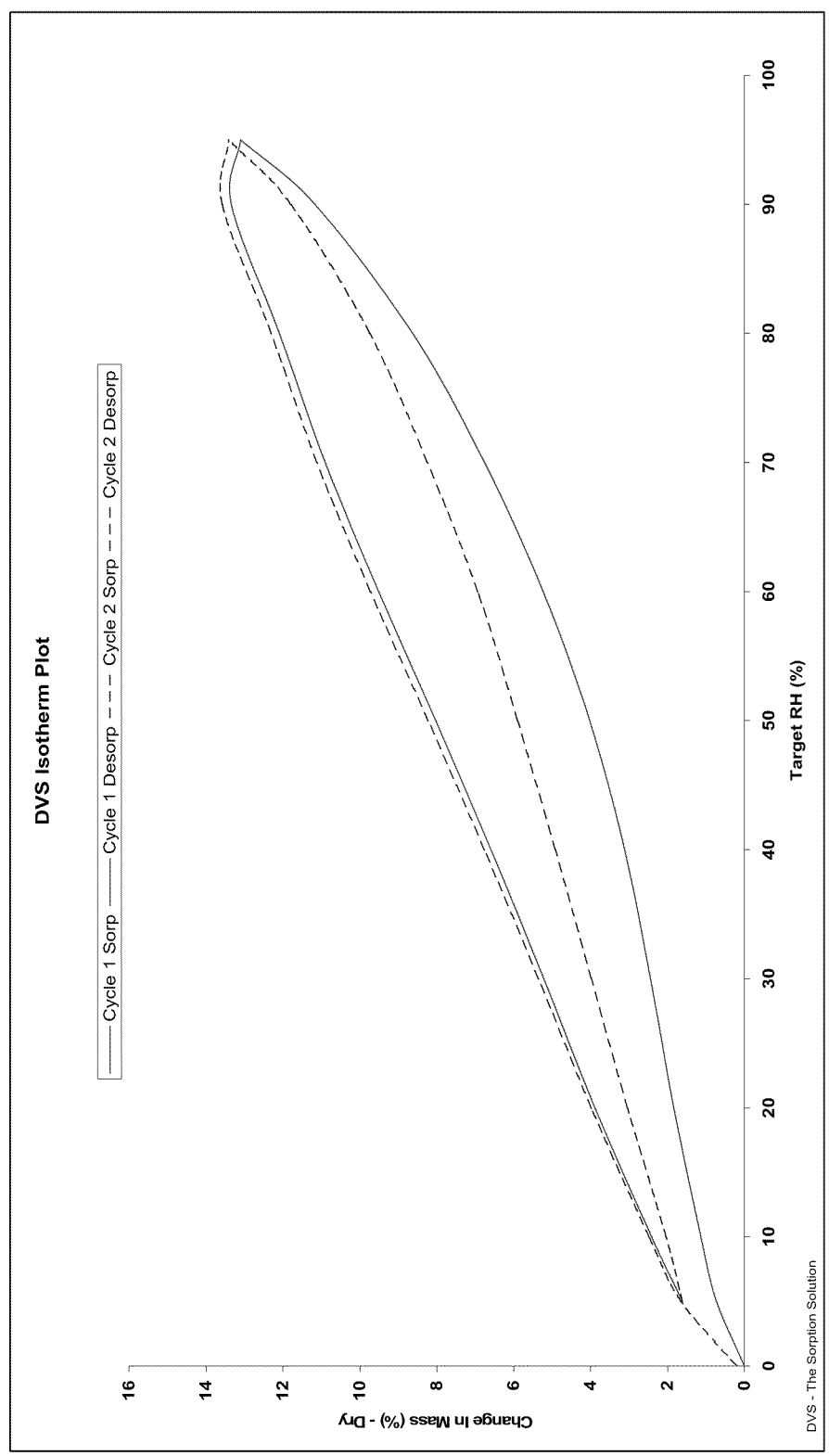
Figure 6: DVS of TMC435 Na salt

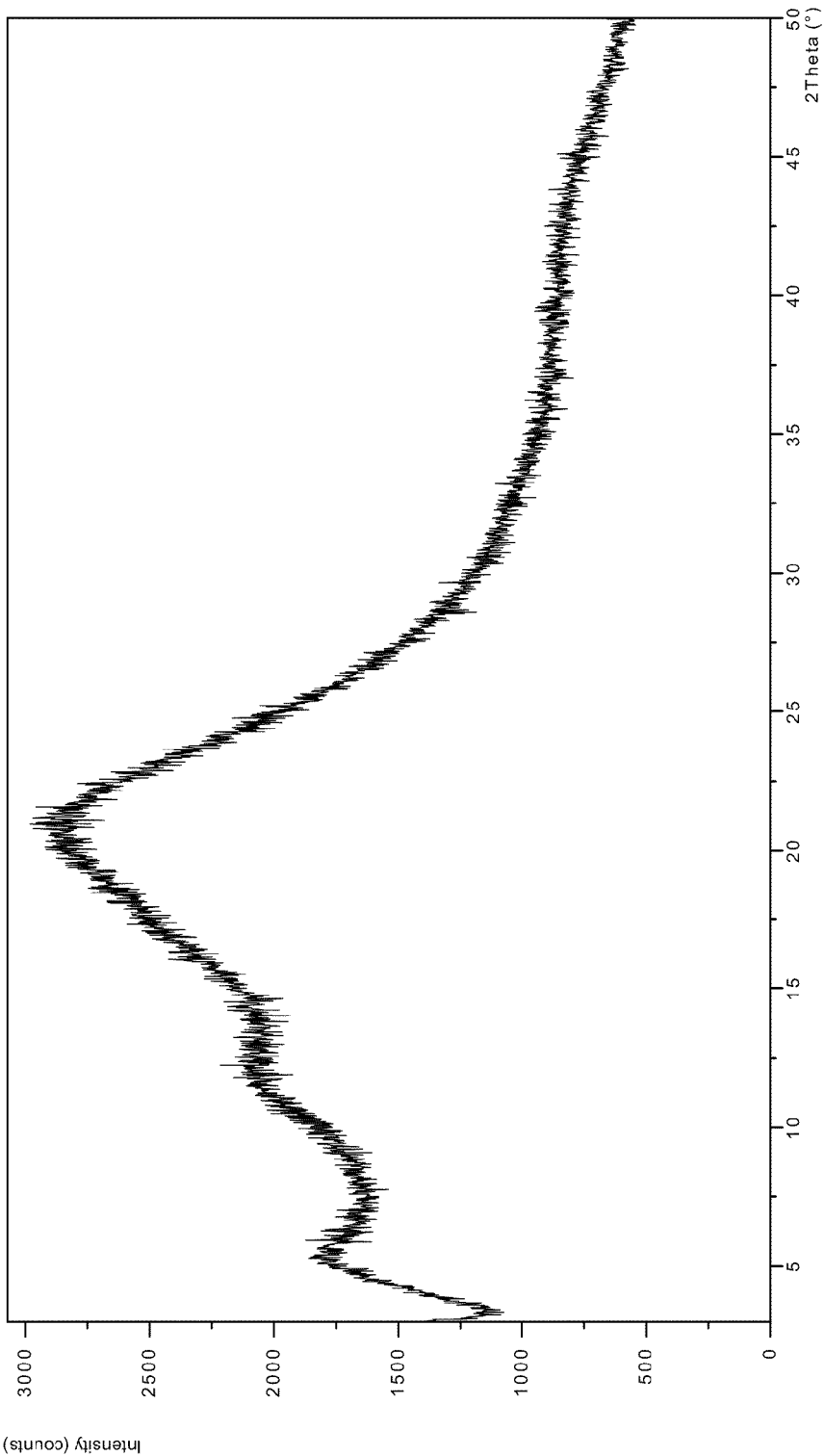
Figure 7: Powder XRD pattern of the amorphous Na salt of TMC435 after storing during 1 year 8 months and 23 days

AMORPHOUS SALT OF A MACROCYCLIC INHIBITOR OF HCV

This application is a national stage application of PCT/EP2010/001197, filed Feb. 26, 2010, which claims priority benefit of Application No. EP 09153964.3 filed Feb. 27, 2009. The complete disclosures of the aforementioned related patent applications are hereby incorporated herein by reference for all purposes.

FIELD OF THE INVENTION

The present invention relates to the sodium salt of a macrocyclic inhibitor of HCV in amorphous form and to a process for preparing this amorphous sodium salt.

BACKGROUND OF THE INVENTION

Infection with the Hepatitis C Virus (HCV) is generally recognized as a major healthcare problem worldwide. HCV infection can progress to liver fibrosis, which can lead to liver cirrhosis, end-stage liver disease, and HCC (hepatocellular carcinoma), making it the leading cause of liver transplantations. Current standard of care in HCV treatment involves the administration of Pegylated interferon-alpha-2a or Pegylated interferon-alpha-2b in combination with ribavirin during 24 or 48 weeks. Current therapy has its limitations in that only part of the patients is treated successfully, in that it faces significant side effects, is often poorly tolerated, and by its long duration. Hence there is a need for HCV inhibitors that overcome these disadvantages.

Replication of the genome of HCV is mediated by a number of enzymes, amongst which is HCV NS3 serine protease. Various agents have been described that inhibit this enzyme. WO 05/073216 discloses linear and macrocyclic NS3 serine protease inhibitors with a central cyclopentane moiety. WO 2007/014926 discloses a series of macrocyclic NS3 serine protease inhibitors, including salt-forms of these compounds. Amongst these, the compound of formula I with the chemical structure depicted hereinafter, is of particular interest. This compound, with its full chemical name (1R,4R,6S,15R,17R)-cis-N-[17-[2-(4-isopropylthiazol-2-yl)-7-methoxy-8-methyl-quinolin-4-yloxy]-13-methyl-2,14-dioxo-3,13-diazatricyclo[13.3.0.0$^{4,6}$]octadec-7-ene-4-carbonyl] (cyclopropyl)sulfonamide or (1R,4R,6S,7Z,15R,17R)-N-[17-[2-(4-isopropylthiazol-2-yl)-7-methoxy-8-methylquinolin-4-yloxy]-13-methyl-2,14-dioxo-3,13-diazatricyclo[13.3.0.0$^{4,6}$]octadec-7-ene-4-carbonyl](cyclopropyl)-sulfonamide, is also referred to as "TMC435". TMC 435 can be prepared by the synthesis procedures described in Example 5 of WO 2007/014926. As used herein, the terms "compound of formula I" and "TMC435" refer to the same chemical entity.

TMC435 not only shows pronounced activity against HCV but also has an attractive pharmacokinetic profile. Clinical investigations show that this compound is well-tolerated in patients and confirm its potential to effectively suppress HCV.

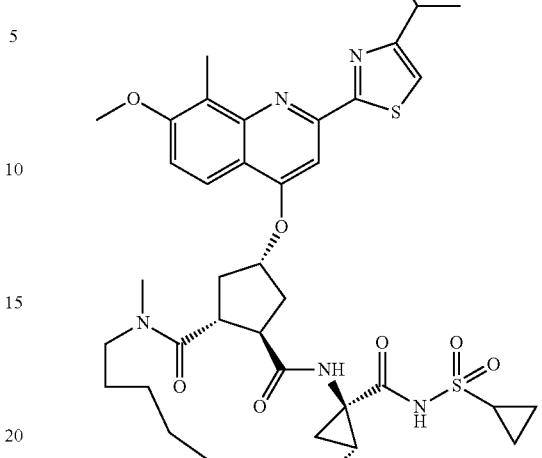

(I)

TMC435 is poorly water-soluble and improving its solubility as well as its concomitant bioavailability are desirable targets for drug development. Administering higher doses of poorly soluble drugs could overcome bioavailability problems, but this leads to larger and therefore less practicable dosage forms. Desired are dosage forms that are compact and easy to manufacture.

It is known that bioavailability of poorly soluble active agents can be improved by converting these in amorphous form. Typically, the more crystalline the pharmaceutical agent, the lower is its bioavailability or vice versa, reducing the degree of crystallinity has a positive effect on bioavailability. Amorphous materials generally offer interesting properties such as a higher dissolution rate and solubility than crystalline forms, typically resulting in improved bioavailability. Generating and stabilizing this state typically proves out to be difficult because for many substances the amorphous form is unstable, quickly converting partially or completely to the more stable crystalline form. This conversion is influenced by external factors such as temperature, humidity, traces of crystalline material in the environment, etc. Even amorphous forms that seem stable for long periods of time can convert partially or completely to crystalline forms, sometimes for reasons that are not immediately clear.

The amorphous and crystalline forms not only show differences in bioavailability, but also in their processing properties, such as hygroscopicity, flowability, compaction, and the like. If during the clinical development and manufacture of solid dosage forms the solid form of the drug substance is not stable, the exact amount of the desired form used or studied may vary from one lot to another causing undesired variability not only in therapeutic efficacy but also in manufacturing conditions. Hence, a drug taken into development will almost always be converted into its crystalline form because of its stability in the manufacture and storage of pharmaceutical dosage forms. Very few drugs therefore are available in the amorphous state.

It is an object of the present invention to provide a solid form of the compound of formula I that is stable and has beneficial properties in terms of one or more of the following: its bioavailability, pharmacokinetic properties such as, release rate, area under the curve, and the like; as well as its ability to be formulated, stored and administered as to effectively exert its antiviral properties.

It now has been found that the sodium salt of the compound of formula I can be converted into its amorphous form, which form is surprisingly stable and can advantageously be used as active ingredient in anti-HCV therapy. This form can be converted into pharmaceutical compositions and dosage forms that are compact and easy to manufacture. It further has been found that this form can conveniently be prepared by spray-drying as manufacturing procedure.

DESCRIPTION OF THE FIGURES

FIG. 1 is an Infrared spectrum (microATR) of the amorphous Na salt of TMC435

FIG. 2 is a Powder XRD (X-ray diffraction) pattern of the amorphous Na salt of TMC435

FIG. 3 is a DSC (differential scanning calorimetry) curve of the amorphous Na salt of TMC435

FIG. 4 is an MDSC (modulated differential scanning calorimetry) overlay of the amorphous Na salt of TMC435

FIG. 5 is a TGA (thermogravimetric analysis) curve of the amorphous Na salt of TMC435

FIG. 6 is a DVS (dynamic vapor sorption) of the amorphous Na salt of TMC435

FIG. 7 is a Powder XRD pattern of the amorphous Na salt of TMC435 stored during 1 year 8 months and 23 days

DESCRIPTION OF THE INVENTION

The present invention relates to the sodium salt of the compound of formula I in amorphous form. The present invention further also to a process for preparing the amorphous form of the sodium salt of the compound of formula I.

In one embodiment, the invention concerns the sodium salt of the compound of formula I in amorphous form, as specified herein, substantially free from impurities. In a particular embodiment, the sodium salt of the compound of formula I in amorphous form contains no more than about 5% of impurities, or no more than about 2% of impurities, or no more than about 1% of impurities, or no more than about 0.5% of impurities, or no more than about 0.1% of impurities. The impurities may be compounds other than the compound of formula I, or may be any of the other solid forms of the compound of formula I, in particular crystalline forms. Purity may be tested by standard spectroscopic techniques, for example with X-ray diffraction.

The present invention also relates to a process for preparing the sodium salt of the compound of formula I in amorphous form, which process comprises the steps of:
a) preparing a mixture of the compound of formula I in a pharmaceutically acceptable non-aqueous solvent and aqueous sodium hydroxide; and
b) spray-drying the mixture of step a) in a spray-drying apparatus.

In one embodiment, step a) comprises mixing a sodium hydroxide solution with the said solvent and subsequently adding the compound of formula I, preferably in its free form, i.e. non-salt form. In a particular embodiment a sodium hydroxide solution in water is added to the solvent, and subsequently, the compound of formula I is added. The procedures of step a) are preferably conducted under stirring. Also preferred is that in step a) the compound of formula I is allowed to form a solution and that this solution is subsequently spray-dried.

The mixture or solution resulting from step a) is then sprayed through the nozzle of a spray-dryer whereby the solvent from the resulting droplets is evaporated, usually at elevated temperatures, e.g. by the introduction of hot air.

In one embodiment, the aqueous sodium hydroxide is a concentrated solution of sodium hydroxide in an aqueous medium, in particular in water, for example a NaOH solution that is in the range of about 1N to about 12.5N, or of about 5N to about 12.5N, or of about 7.5N to about 12.5N, for example is about 10 N.

Solvents that can be used in this process are those that are accepted for use in the preparation of pharmaceutical compositions and are both volatile enough for use in spray-drying (with a boiling point below e.g. 150° C., or below e.g. 100° C.) and can sufficiently dissolve TMC435 (having a TMC435 solubility of e.g. >10 g/l, or e.g. >50 g/l). Suitable solvents comprise halogenated hydrocarbons, such as chloroform or preferably, dichloromethane; or ethers such as diethylether or tetrahydrofuran. The drying gas may be any gas. Preferably, the gas is air or an inert gas such as nitrogen, nitrogen-enriched air or argon. The temperature of the drying gas at the gas inlet of the spray-drying chamber can be from about 25° C. to about 300° C., or from about 60° C. to about 300° C., or from about 60° C. to about 150° C.

The spray-drying is conducted in a conventional spray-drying apparatus comprising a spray-drying chamber, atomizing means for introducing the feed mixture into the spray-drying chamber in the form of droplets, a source of heated drying gas that flows into the spray-drying chamber through an inlet, and an outlet for the heated drying gas. The spray-drying apparatus also comprises a means for collecting the solid pharmaceutical powder that is produced. The atomizing means can be a rotary atomizer, a pneumatic nozzle, an ultrasonic nozzle or, preferably, a high-pressure nozzle.

Suitable rotary atomizers include those having an air turbine drive operating from a high pressure compressed air source, for example a 6 bar compressed air source, which supplies power to an atomization wheel for atomizing the feed mixture. The atomization wheel may be vaned. Preferably, the rotary atomizer is located in the upper part of the spray-drying chamber, for example in the chamber roof, so that the droplets produced dry and fall to the lower part of the chamber. Typically, rotary atomizers produce droplets that have a size in the range of from about 20 to about 225 μm, in particular from about 40 to about 120 μm, the droplet size depending upon the wheel peripheral velocity.

Suitable pneumatic nozzles (including two-fluid nozzles) comprise those that are located in the upper part of the spray-drying chamber, for example in the chamber roof, and operate in so-called "co-current mode". Atomization takes place using compressed air such that the air-liquid ratio is in the range of about 0.5-1.0:1 to about 5:1, in particular from about 1:1 to about 3:1. The feed mixture and the atomizing gas are passed separately to the nozzle head, where the atomization takes place. The size of the droplets produced by pneumatic nozzles depends on the operating parameters and can be in the range e.g. from about 5 to 125 μm, or from about 20 to 50 μm.

Two-fluid nozzles that operate in so-called "counter-current mode" may also be used. These nozzles operate in a similar way to two-fluid nozzles in co-current modes except that they are located in a lower part of the drying chamber and spray droplets upwards. Typically, counter-current two-fluid nozzles generate droplets, which, when dried, produce particles having a size in the ranging from about 15 to about 80 p.m.

Suitable ultrasonic atomizer nozzles convert low viscosity liquids into ultra fine sprays. As liquids are pumped through the center of the probe, the liquids are mechanically pulverized into droplets from the vibrating tip. These droplets are larger with low frequency probes and smaller with higher frequency probes.

A preferred atomizer type for use in the invention is the high-pressure nozzle where liquid feed is pumped to the nozzle under pressure. Pressure energy is converted to kinetic energy, and feed issues from the nozzle orifice as a high-speed film that readily disintegrates into a spray as the film is unstable. The feed is made to rotate within the nozzle using a swirl insert or swirl chamber resulting in cone-shaped spray patterns emerging from the nozzle orifice. Swirl insert, swirl chamber and orifice dimensions together with variation of pressure gives control over feed rate and spray characteristics. The size of the droplets produced by high-pressure nozzles depends on the operating parameters and can be in the range from about 5 to 125 mm, e.g. from about 20 to about 50 mm.

Suitable atomizing means may be selected depending on the desired droplet size, which depends on a number of factors, such as the viscosity and temperature of the feed mixture, the desired flow rate and the maximum acceptable pressure to pump the feed mixture, have on droplet size. After selecting the atomizing means so that the desired average droplet size is obtained for a feed mixture having a particular viscosity, the mixture is admitted to the spray-drying chamber at a particular flow rate.

The powder obtained after the spray-drying step may further be dried, for example at increased temperature, or at reduced pressure, or both.

The processes described herein provide convenient procedures to prepare the amorphous sodium salt of TMC435 in very high yield and with a high degree of purity (both close to 100%, such as for example the yield and being >95%, or >99%, these percentages in the instance of purity being w/w, i.e. weight/weight). Small amounts of water can be present in the obtained product after drying, for example from about 5% to about 1%, w/w. When brought into contact with humidity, up to about 13% (in particular about 13.1%) can be absorbed. Even when water is absorbed, the product remains stable.

The resulting powder, after addition of the required excipients, can be processed directly into solid dosage forms such as tablets or capsules.

In still a further aspect, the invention provides the amorphous form of the sodium salt of the compound of formula I, obtained or obtainable by a spray-drying process as described herein.

The present invention also relates to the sodium salt of the compound of formula I in amorphous form for use as a medicament. This invention also relates to the sodium salt of the compound of formula I in amorphous form for use as a HCV inhibitor, or for use for the treatment of HCV-related conditions. The invention also relates to the use of the sodium salt of the compound of formula I in amorphous form in the manufacture of a medicament for inhibiting HCV, or for the treatment of HCV-related conditions.

The present invention also concerns a method of treating a mammal, in particular a human, suffering from HCV infection, or suffering from conditions associated with HCV infection, said method comprising administering the amorphous sodium salt of the compound of formula I to a mammal in need thereof.

HCV-related conditions include those pathologic conditions brought on by HCV, including progressive liver fibrosis, inflammation and necrosis leading to cirrhosis, end-stage liver disease, and HCC. The amount to be administered in particular is an effective amount, this referring to an amount that is effective in suppressing or reducing HCV infection, or suppressing or reducing the conditions associated with HCV infection. Preferably, said amount is selected such that the viral load drops significantly, e.g. the viral load drops at least two orders of magnitude, or the viral load drops at least three orders of magnitude, or the viral load drops at least four orders of magnitude, or the viral load drops below the detection limit of HCV.

In addition, the invention provides a pharmaceutical composition comprising the sodium salt of the compound of formula I in amorphous form and a pharmaceutically acceptable carrier. The said sodium salt of the compound of formula I in amorphous form preferably is present in the said pharmaceutical composition in an effective amount, i.e. an amount as specified above.

The pharmaceutically acceptable carrier present in the pharmaceutical compositions of the invention may comprise one or more pharmaceutically acceptable excipients. The said pharmaceutical compositions preferably are in solid form but may also be in liquid or semi-liquid form, in which case the compound of formula I in amorphous form is present as a suspension. Pharmaceutically acceptable excipients comprise solid carriers such as binders, fillers, starches, diluents, lubricants, binders, disintegrants, and the like. Binders comprise starches, gelatin, cellulose and its derivatives, natural and synthetic gums such as guar gum, gum Arabic, etc. Fillers comprise talc, calcium carbonate, microcrystalline cellulose, powdered cellulose, kaolin, mannitol, sorbitol, starch, etc. Disintegrants comprise agar-agar, alginic acid, calcium carbonate, microcrystalline cellulose, croscarmellose sodium, crospovidone, pre-gelatinized starch, etc. Lubricants comprise oils, e.g. vegetable or animal oils, such as sunflower oil or cod liver oil, magnesium stearate, zinc stearate, mannitol, sorbitol, searic acid, sodium lauryl sulfate, talc, agar, etc.

Pharmaceutical compositions may be prepared as dosage forms to be administered orally, which is preferred, or parenterally (including subcutaneously, intramuscularly, and intravenously), rectally, transdermally, bucally, or nasally. Suitable forms for oral administration include powders, granulates, aggregates, tablets, caplets, compressed or coated pills, dragees, sachets, hard or gelatin capsules, and suspensions. Suitable forms for parenteral administration include various aqueous or non-aqueous suspensions. In this instance the particles that are suspended are of sufficient small size as to allow parenteral administration. For nasal delivery there are provided suitable art-known aerosol delivery systems. The compositions may be conveniently presented in unit dosage form, in particular tablets and capsules. Alternatively, the dosage forms may be presented as one, two, three, four, or more subdoses administered at appropriate intervals throughout the day.

The sodium salt of the compound of formula I in amorphous form, either as such or in the form of a pharmaceutical composition or, preferably, as unit dosage form, is preferably administered once daily (q.d.). Other dosage regimens may also be applied, for example twice or three times daily. A suitable daily dosage of the sodium salt of the compound of formula I in amorphous form, expressed as amounts of the free form of the compound of formula I, per day, is from about 1 mg to about 1000 mg of the compound of formula I, or from about 5 to about 800 mg, or from about 5 to about 400 mg, or from about 10 to about 300 mg, or from about 20 to about 250 mg, or from about 50 to about 200 mg, for example about 25 mg, or about 75 mg, or about 100 mg, or about 150 mg, or about 200 mg. To calculate the daily amount of the amorphous sodium salt to be administered, each of the cited values has to be multiplied by 1.029, or by 1.0293.

The unitary dosage forms as described herein will contain amounts of the sodium salt of the compound of formula I in amorphous form that are equal to the amounts mentioned above.

In addition to the ingredients mentioned above, the pharmaceutical compositions of the present invention may include other agents conventional in the art having regard to the type of composition in question, for example those suitable for oral administration may include flavoring agents or taste masking agents.

The invention also relates to a combination of the sodium salt of the compound of formula I in amorphous form and another antiviral compound, in particular another anti-HCV compound. The term "combination" may relate to a product containing (a) the sodium salt of the compound of formula I in amorphous form, as specified herein, and (b) optionally another anti-HCV compound, as a combined preparation for simultaneous, separate or sequential use in treatment of HCV infections.

Anti-HCV compounds that can be used in such combinations include HCV polymerase inhibitors, HCV protease inhibitors, inhibitors of other targets in the HCV life cycle, and an immunomodulatory agents, and combinations thereof. HCV polymerase inhibitors include, NM283 (valopicitabine), R803, JTK-109, JTK-003, HCV-371, HCV-086, HCV-796 and R-1479, R-7128, MK-0608, VCH-759, PF-868554, GS9190, XTL-2125, NM-107, GSK625433, R-1626, BILB-1941, ANA-598, IDX-184, IDX-375, MK-3281, MK-1220, ABT-333, PSI-7851, PSI-6130, VCH-916. Inhibitors of HCV proteases include BILN-2061, VX-950 (telaprevir), GS-9132 (ACH-806), SCH-503034 (boceprevir), ITMN-191, MK-7009, BI-12202, BILN-2065, BI-201335, BMS-605339, R-7227, VX-500, BMS650032, VBY-376, VX-813, SCH-6, PHX-1766, ACH-1625, IDX-136, IDX-316. An example of an HCV NS5A inhibitor is BMS790052, A-831, A-689, NIM-811 and DEBIO-025 are examples of NS5B cyclophilin inhibitors.

Inhibitors of other targets in the HCV life cycle, including NS3 helicase; metallo-protease inhibitors; antisense oligonucleotide inhibitors, such as ISIS-14803 and AVI-4065; siRNA's such as SIRPLEX-140-N; vector-encoded short hairpin RNA (shRNA); DNAzymes; HCV specific ribozymes such as heptazyme, RPI.13919; entry inhibitors such as HepeX-C, HuMax-HepC; alpha glucosidase inhibitors such as celgosivir, UT-231B and the like; KPE-02003002; and BIVN 401.

Immunomodulatory agents include, natural and recombinant interferon isoform compounds, including α-interferon, β-interferon, γ-interferon, and ω-interferon, such as Intron A®, Roferon-A®, Canferon-A300®, Advaferon®, Infergen®, Humoferon®, Sumiferon MP®, Alfaferone®, IFN-beta®, and Feron®; polyethylene glycol derivatized (pegylated) interferon compounds, such as PEG interferon-α-2a (Pegasys®), PEG interferon-α-2b (PEG-Intron®), and pegylated IFN-α-con1; long acting formulations and derivatizations of interferon compounds such as the albumin-fused interferon albuferon α; compounds that stimulate the synthesis of interferon in cells, such as resiquimod; interleukins; compounds that enhance the development of type 1 helper T cell response, such as SCV-07; TOLL-like receptor agonists such as CpG-10101 (actilon), and isatoribine; thymosin α-1; ANA-245; ANA-246; histamine dihydrochloride; propagermanium; tetrachlorodecaoxide; ampligen; IMP-321; KRN-7000; antibodies, such as civacir and XTL-6865; and prophylactic and therapeutic vaccines such as InnoVac C and HCV E1E2/MF59.

Other antiviral agents include, ribavirin, amantadine, viramidine, nitazoxanide; telbivudine; NOV-205; taribavirin; inhibitors of internal ribosome entry; broad-spectrum viral inhibitors, such as IMPDH inhibitors, and mycophenolic acid and derivatives thereof, and including, but not limited to, VX-497 (merimepodib), VX-148, and/or VX-944); or combinations of any of the above.

Particular agents for use in said combinations include interferon-α (IFN-α), pegylated interferon-α (in particular pegylated interferon-α-2a and -α-2b), and ribavirin, as well as therapeutics based on antibodies targeted against HCV epitopes, small interfering RNA (Si RNA), ribozymes, DNAzymes, antisense RNA.

In another aspect there are provided combinations of the sodium salt of the compound of formula I in amorphous form as specified herein and an anti-HIV compound. The latter preferably are those HIV inhibitors that have a positive effect on drug metabolism and/or pharmacokinetics that improve bioavailabilty. An example of such an HIV inhibitor is ritonavir.

The said combinations may find use in the manufacture of a medicament for treating HCV infection in a mammal infected therewith, said combination in particular comprising the sodium salt of the compound of formula I in amorphous form, as specified above and interferon-α (IFN-α), pegylated interferon-α (in particular pegylated interferon-α-2a and -α-2b), or ribavirin. Or the invention provides a method of treating a mammal, in particular a human, infected with HCV comprising the administration to said mammal of an effective amount of a combination as specified herein. In particular, said treating comprises the systemic administration of the said combination, and an effective amount is such amount that is effective in treating the clinical conditions associated with HCV infection.

In one embodiment the above-mentioned combinations are formulated in the form of a pharmaceutical composition that includes the active ingredients described above and a carrier, as described above. Each of the active ingredients may be formulated separately and the compositions may be co-administered, or one composition containing both, and if desired further, active ingredients may be provided. In the former instance, the combinations may also be formulated as a combined preparation for simultaneous, separate or sequential use in HCV therapy. The said composition may take any of the forms described above. In one embodiment, both ingredients are formulated in one dosage form such as a fixed dosage combination. In a particular embodiment, the present invention provides a pharmaceutical composition comprising (a) a therapeutically effective amount of the sodium salt of the compound of formula I in amorphous form, (b) a therapeutically effective amount of another HCV inhibitor, such as those mentioned above, and (c) a carrier. The carrier may comprises any of the ingredients mentioned above.

The individual components of the combinations of the present invention can be administered separately at different times during the course of therapy or concurrently in divided or single combination forms. The present invention is meant to embrace all such regimes of simultaneous or alternating treatment and the term "administering" is to be interpreted accordingly. In a preferred embodiment, the separate dosage forms are administered simultaneously.

The amorphous sodium salt of TMC435 is stable during long periods of time, i.e. periods exceeding 1½ years, as can be demonstrated by comparing the XRD spectra taken shortly after its preparation and after a long period of time. FIG. 7 shows the Powder XRD pattern of the amorphous Na salt of TMC435 after storing during 1 year, 8 months and 23 days. This pattern remained essentially unchanged as compared to the pattern obtained shortly after the preparation of TMC435

Na salt, as represented in FIG. 2. This means that the amorphous Na salt of TMC435 allows stable storage during a normal shelf life period.

As used herein, the term "about" has its conventional meaning. In certain embodiments when in relation to a numerical value, it may be interpreted to mean the numerical value±10%, or ±5%, or ±2%, or ±1%, or ±0.5%, or ±0.1%. In other embodiments, the word "about" is left out so as to indicate that the precise value is meant.

EXAMPLES

The following examples are intended to illustrate the present invention and not to limit it thereto.

Example 1

Preparation of the Sodium Salt of TMC435 in Amorphous Form

Sodium hydroxide 10 N solution, prepared by dissolving 24.00 g sodium hydroxide in 55.80 g purified water, was added to 5949.00 g vigorously stirred methylene chloride. TMC435 (450.00 g) was added to this mixture under moderate stirring, and stirring was continued until the resulting mixture was visually clear. The thus obtained mixture was spray dried in a standard spray dryer under $N_2$ conditions. The spray dried product was collected and dried in a vacuum oven. The resulting powder being the amorphous sodium salt of TMC435, contained the free form of the active ingredient TMC435 in an amount of 971.53 mg/g powder.

Example 2

Preparation of TMC435 Oral Capsules

The spray dried powder (72.05 g) obtained in example 1, sodium laurylsulfate (1.19 g), anhydrous colloidal silica (1.19 g) and lactose monohydrate (158.83 g) were sieved and blended in a suitable recipient for 10 minutes. Sieved magnesium stearate (1.19 g) was added to this mixture and the resulting mixture was blended for 5 more minutes. The resulting composition was filled into hard gelatin capsules.

Table 1 presents the batch formula for a typical batch size of 700 capsules in the manufacturing of amorphous TMC435 sodium salt oral capsules.

| Component | Quantity (mg) per capsule | Quantity (g) per Batch Size of 700 capsules |
|---|---|---|
| amorphous TMC435 sodium salt | 102.93 mg | 72.05 g |
| Sodium lauryl sulphate | 1.7 mg | 1.19 g |
| Magnesium stearate | 1.7 mg | 1.19 g |
| Silica colloidal anhydrous | 1.7 mg | 1.19 g |
| Lactose monohydrate | 226.9 mg | 158.83 g |
| Hard gelatin capsule - size 0 - cap red5/body red5 | 1 pc | 700 pcs |

Table 2 presents the batch formula for a typical batch size of 600 capsules in the manufacturing of amorphous TMC435 sodium salt 25 mg oral capsules.

| Component | Quantity (mg) per capsule | Quantity (g) per Batch Size of 600 capsules |
|---|---|---|
| amorphous TMC435 sodium salt | 25.73 mg | 15.44 g |
| Sodium lauryl sulphate | 0.4 mg | 0.24 g |
| Magnesium stearate | 0.4 mg | 0.24 g |
| Silica colloidal anhydrous | 0.4 mg | 0.24 g |
| Lactose monohydrate | 51.8 mg | 31.08 g |
| Hard gelatin capsule - size 4 - cap red5/body red 5 | 1 pc | 600 pcs |

Example 3

Characterization of the Amorphous Sodium Salt Prepared According to Example 1

Amorphous
Showed a glass transition at 192.5° C.
Contained solvent (water)
  DSC showed an endothermic signal at 81.1° C. (78 J/g)
  TGA showed a weight loss of 3.7% (25-245° C.)
Hygroscopic
Infrared Spectrometry (IR)
Micro Attenuated Total Reflectance (microATR)
  The sample was analyzed using a suitable microATR accessory.

| | |
|---|---|
| number of scans: | 32 |
| resolution: | $1 \text{ cm}^{-1}$ |
| wavelength range: | 4000 to 400 $\text{cm}^{-1}$ |
| apparatus: | Thermo Nexus 670 FTIR spectrophotometer |
| baseline correction: | yes |
| detector: | DTGS with KBr windows |
| beamsplitter: | Ge on KBr |
| micro ATR accessory: | Harrick Split Pea with Si crystal |

The IR spectrum of TMC435 Na salt contained solvent (water) and reflects the vibrational modes of the molecular structure of the sodium salt of TMC435.
IR spectrum See FIG. 1
Powder XRD
  X-ray powder diffraction (XRPD) analysis was carried out on a Philips X'PertPRO MPD diffractometer PW3050/60 with generator PW3040. The instrument was equipped with a Cu LFF X-ray tube PW3373/10. The compound was spread on a zero background sample holder.
Instrument Parameters

| | |
|---|---|
| generator voltage: | 45 kV |
| generator amperage: | 40 mA |
| geometry: | Bragg-Brentano |
| stage: | spinner stage |

Measurement Conditions

| | |
|---|---|
| scan mode: | continuous |
| scan range: | 3 to 50° 2θ |
| step size: | 0.0167°/step |
| counting time: | 29.845 sec/step |
| spinner revolution time: | 1 sec |
| radiation type: | CuKα |
| radiation wavelength: | 1.5406 Å |

Incident Beam Path

| | |
|---|---|
| program. divergence slit: | 15 mm |
| Soller slit: | 0.04 rad |
| beam mask: | 15 mm |
| anti scatter slit: | 1° |
| beam knife: | + |

Diffracted Beam Path

| | |
|---|---|
| long anti scatter shield: | + |
| Soller slit: | 0.04 rad |
| Ni filter: | + |
| detector: | X'Celerator |

The X-ray powder diffraction pattern of the amorphous TMC435 sodium salt showed only the presence of a halo, indicating that this compound was present as an amorphous product.

XRD pattern See FIG. 2

Differential Scanning Calorimetry (DSC)

About 3 mg of the compound was transferred into a standard aluminum TA-Instrument sample pan. The sample pan was closed with a cover and the DSC curve was recorded on a TA-Instruments Q1000 MTDSC equipped with a RCS cooling unit.

Parameters

| | |
|---|---|
| initial temperature: | 25° C. |
| heating rate: | 10° C./min |
| final temperature: | 300° C. |
| nitrogen flow: | 50 ml/min |

The DSC curve of TMC435 sodium salt showed an endothermic signal at 81.1° C. (77 J/g) due to solvent evaporation.

A second event was observed at ±199.4° C. and is probably related to the glass transition (Tg), the relaxation energy and/or to the evaporation of solvent.

DSC curve See FIG. 3

Modulated Differential Scanning Calorimetry (MDSC)

About 3 mg of amorphous TMC435 sodium salt was transferred into a standard aluminum TA-Instrument sample pan. The sample pan was closed with a cover and the DSC curve was recorded on a TA-Instruments Q1000 MTDSC equipped with a RCS cooling unit.

Parameters

| | |
|---|---|
| Mode: | T4P |
| nitrogen flow: | 50 ml/min |
| equilibrate at: | −60° C. |
| modulate: | heat only 60 s |
| ramp: | 2° C./min |
| Final temperature: | 225° C. |

An MDSC experiment was conducted to determine the glass transition (Tg) (shift in specific heat) of the sample. In general, MDSC experiments can separate the evaporation of solvent and the relaxation energy, which are kinetic processes (non-reversing heat flow signal) from the change in heat capacity (reversing heat flow signal). The (total) heat flow is comparable to a standard DSC signal. If a non-hermetic sample pan was used for the amorphous TMC435 sodium salt, the MDSC curve showed the evaporation of the solvent present at ±46.9° C. clearly separated from the glass transition at ±192.5° C.

MDSC overlay See FIG. 4.

Thermogravimetry (TGA)

Amorphous TMC435 was transferred into an aluminum sample pan. The TG curve was recorded on a TA Instruments Q500 thermogravimeter.

Parameters

| | |
|---|---|
| initial temperature: | room temperature |
| heating rate: | 20° C./min |
| resolution factor: | 4 |
| final condition: | 300° C. or <80[(w/w)%] |

For amorphous TMC435 sodium salt, a weight loss of ±3.7% was registered in the temperature region from room temperature up to 245° C. and was due to the evaporation of solvent (water) present in the sample. The loss of weight above 250° C. was due to the decomposition of the product.

TGA curve See FIG. 5

Adsorption-Desorption (DVS)

Amorphous TMC435 (19 mg) was transferred into a SMS (Surface Measurement Systems Ltd.) dynamic vapor sorption model DVS-1 and the weight change was recorded with respect to the atmospheric humidity at 25° C.

Parameters

| | |
|---|---|
| drying: | 60 min under dry nitrogen |
| equilibrium: | ≤0.01%/min for minimal 15 min and maximal 60 min. |
| data interval: | 0.05% or 2.0 min |
| | Measurements were made at the following relative humidity (RH (%)) levels: |
| first set: | 5, 10, 20, 30, 40, 50, 60, 70, 80, 90, 95, 90, 80, 70, 60, 50, 40, 30, 20, 10, 5 |
| second set: | 5, 10, 20, 30, 40, 50, 60, 70, 80, 90, 95, 90, 80, 70, 60, 50, 40, 30, 20, 10, 5, 0 |

During the initial drying step, a weight loss of 2.03% was registered for the sodium salt of compound I. The obtained dried product was hygroscopic and adsorbed up to 13.1% water at high relative humidity. During the desorption cycle 1.61% moisture remained on the product.

The obtained product after DVS was investigated with IR and XRD and remained amorphous.

ADS/DES curve See FIG. 6.

The invention claimed is:

1. A process for preparing a sodium salt of the compound in solid amorphous form comprising:
   (a) preparing a mixture of the compound of formula I in dichloromethane and aqueous sodium hydroxide; and
   (b) spray-drying a mixture of (a) in a spray-drying apparatus; wherein said compound is of formula I:

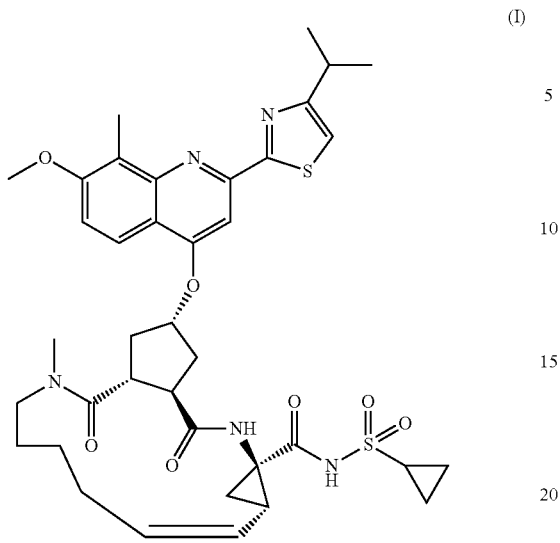
wherein the aqueous sodium hydroxide is from about 7.5N to about 12.5N sodium hydroxide solution in water.
2. The process of claim 1 wherein step a) comprises mixing a sodium hydroxide solution in water with the said solvent and subsequently adding the compound of formula I.
3. The process of claim 2, wherein in step a) the compound of formula I is allowed to form a solution.
* * * * *